Figure 1:
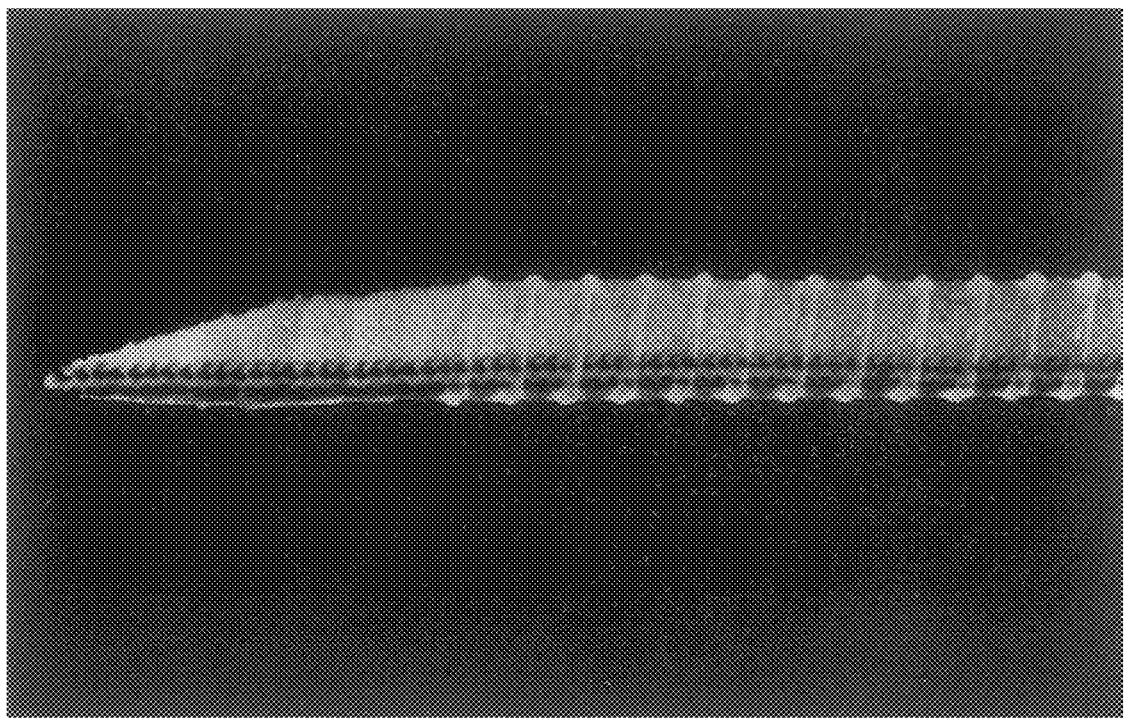

United States Patent [19]
Angelini

[11] Patent Number: 6,071,306
[45] Date of Patent: Jun. 6, 2000

[54] EXTERNALLY STENTED VEIN SEGMENT AND ITS USE IN AN ARTERIOVENOUS BYPASS GRAFTING PROCEDURE

[75] Inventor: Gianni Angelini, Bristol, United Kingdom

[73] Assignee: University of Bristol, Bristol, United Kingdom

[21] Appl. No.: 08/961,424

[22] Filed: Oct. 30, 1997

Related U.S. Application Data

[63] Continuation of application No. 08/615,345, Mar. 11, 1996, abandoned.

[30] Foreign Application Priority Data

Mar. 9, 1995 [GB] United Kingdom .................. 9504758

[51] Int. Cl.$^7$ ........................................................ A61F 2/00
[52] U.S. Cl. ............................................................ 623/1.13
[58] Field of Search ................................... 623/1, 11, 12, 623/66, 901, 1.13; 128/898; 606/151, 153, 154, 158; 424/422, 423, 424, 425, 426

[56] References Cited

U.S. PATENT DOCUMENTS

| | | | |
|---|---|---|---|
| Re. 31,618 | 7/1984 | Mano et al. ................................. | 623/1 |
| 3,626,947 | 12/1971 | Sparks ................................. | 128/334 R |
| 3,974,526 | 8/1976 | Dardik et al. ................................. | 623/1 |
| 4,546,500 | 10/1985 | Bell ................................................... | 623/1 |
| 4,629,458 | 12/1986 | Pinchuk ...................................... | 623/1 |
| 4,743,251 | 5/1988 | Barra . | |
| 5,246,452 | 9/1993 | Sinnott ......................................... | 623/1 |
| 5,298,276 | 3/1994 | Jayaraman ................................... | 427/2 |

FOREIGN PATENT DOCUMENTS

| | | |
|---|---|---|
| 1 195 992 | 6/1970 | United Kingdom . |
| WO 82 04390 | 12/1982 | WIPO . |
| WO 93 21860 A1 | 11/1993 | WIPO . |
| WO 93/21860 | 11/1993 | WIPO . |
| WO 94/13224 | 6/1994 | WIPO . |
| WO 94/13224 A1 | 6/1994 | WIPO . |
| WO 95 15130 A1 | 6/1995 | WIPO . |
| WO 95/15130 | 6/1995 | WIPO . |
| WO 95 35072 A2 | 12/1995 | WIPO . |
| WO 95/35072 | 12/1995 | WIPO . |

OTHER PUBLICATIONS

A. Moritz et al., "Die Verwendung schlauchumhullter dilatierter oder varikoser Venen als arterielles Bypassransplantat", Vasa Suppl, 1992, 37, p. 20.

A. Moritz et al., "Ummantelte dilatierte oder varikose Venen als arterielles Bypasstransplantat: Experimentelle und erste klinische Ergebnisse", Vasa 1991, 20(3) p. 222–229.

A. Moritz et al., "Improved Biocompatiblilty by Postifixation Treatment of Aldehyde Fixed Bovine Pericardium", ASA 10 Trans. Jul–Sep. 1990, 36(3) p. M300–3.

W. Trubel, "Compliance and Formation of Distal Anastomotic Intimal Hyperplasia in Dacron Mesh Tube Constricted Veins Used as Arterial Bypass Grafts", ASA10 Journal 1994, pp. M273–278.

R. Guidon et al., "New Polyester Arterial Prostheses from Great Britian: An In Vitro and In Vivo Evaluation", Annals of Biomedical Engeering, 1986; pp. 351–367.

B. Buxton et al., "Practical Consideration in Fabric Vascular Grafts", The American Journal of Surgery, 1973, pp. 288–293.

A. Moritz et al., "Mesh Tube–Calibrated Varicose Veins for Coronary Artery Bypass Grafting", Ann Thorac Surg. 1994; pp. 240–242.

(List continued on next page.)

*Primary Examiner*—Michael J. Milano
*Attorney, Agent, or Firm*—Fish & Richardson P.C.

[57] ABSTRACT

There is disclosed an arteriovenous bypass grafting procedure in which a vein segment is implanted into the arterial circulation of a mammalian subject, wherein a non-restrictive porous stent is provided around the grafted vein.

32 Claims, 3 Drawing Sheets

OTHER PUBLICATIONS

A. Moritz et al., "Mesh Tube–Constricted Varicose Veins Used as Bypass Grafts for Infrainguinal Arterial Vascular Reconstruction", Arch. Surg. 1994, pp. 416–420.

A. Moritz et al., "A Method for Constricting Large Veins for Use in Arterial Vascular Reconstruction", Artif Organs, 1990, pp. 394–399.

A. Moritz et al., "Mesh–constricted varicose and dilated veins used as arterial bypass grafts", The International Journal of Artificial Organs, 1991, pp. 435–440.

Buxton, B. F. et al., "Practical Considerations in Fabric Vascular Grafts", The American Journal of Surgery, vol. 125, No. 3, Mar. 1973, pp. 288–293.

Moritz, A. et al., "Use of Prosthesis Enclosed Dilated or Varicose Veins As Arterial Bypass Transplant", II. Chirurgische Universitatsklinik Wien, 1992, 37 p. 20, ISSN: 0251–1029, Switzerland.

Moritz, A. et al., "Stented Dilated or Varicose Veins As Arterial Bypass Transplants: Experimantal and Initial Clinical Results", II. Chirugische Universitatsklinik Wien, 1991, 20 pp. 22–9, ISSN: 0301–1526, Switz.

Trubel, W. et al., "Compliance and Formation of Distal Anastomotic Intimal Hyperplasia in Dacron . . . ", ASAIO Journal 1994, pp. M273–M278.

Guidoin, R. G. et al., "New Polyseter Arterial Prosthesis From Great Britian: An In Vitro and In Vivo Evaluation", Annals of BIomedical Engineering, vol. 14, pp. 351–367, 1986, USA.

Buxton, B. F. et al., "Practical Considerations in Fabric Vascular Grafts", The American Journal of Surgery, pp. 288–293, USA.

Moritz, A. et al., "Mesh Tube–Calibrated Varicose Veins for Coronary Artery Bypass Grafting", The Society of Thoractic Surgeons, pp. 240–242, 1994, Vienna, Austria.

Moritz, A. et al., "Mesh Tube–Constricted Varicose Veins Used as Bypass Grafts for Infraiguinal Arterial Reconstruction", Arch. Surg., vol. 172, Apr. 1992, pp. 416–420.

Moritz, A. et al., "A Method for Constricting Large Veins for Use in Arterial Vascular Reconstruction", Artif Organs, vol. 14, No. 5, 1990, pp. 394–399.

Moritz, A. et al., "Mesh–Constrticted Varicose and Dilated Veins Used As Arterial Bypass Grafts", The International Journal of Artificial Organs, vol. 14, No. 7, 1991, pp. 435–440.

Moritz, A. et al., "Improved Biocompatibility by Postfixation Treatment of Aldehyde Fixed Bovine Pericardium", II, Chirurgische Universitatsklinik, University of Vienna, pp. M300–M303.

EXTERNALLY STENTED VEIN SEGMENT AND ITS USE IN AN ARTERIOVENOUS BYPASS GRAFTING PROCEDURE

This application is a continuation of U.S. application Ser. No. 08/615,345, filed Mar. 11, 1996, now abandoned.

This invention relates to an improvement in arteriovenous grafting.

Bypass of stenotic coronary arteries with autologous saphenous vein has become an established treatment for end-stage atherosclerotic disease, with more than 400,000 procedures in the United States alone each year. The long-term clinical success of coronary bypass grafting is limited, however, by occlusion of up to 50% of grafts within 10 years. Late occlusion results from progressive medial and neointimal thickening with superimposed vein graft atherosclerosis. Apart from lipid lowering therapy, no pharmacological or surgical intervention has been shown conclusively to influence the evolution of these changes either in man or in experimental models.

According to a first aspect of this invention, there is provided an arteriovenous bypass grafting procedure in which a vein segment is implanted into the arterial circulation of a mammalian subject, wherein a non-restrictive porous stent is provided around the grafted vein.

According to a second aspect of this invention, there is provided an externally stented vein segment for use in an arteriovenous bypass grafting procedure, said vein segment having provided about its outer peripheral surface a non-restrictive porous stent.

In the arteriovenous bypass grafting procedure of the present invention, the vein segment is implanted into the arterial circulation of a mammalian subject. This will include the coronary artery, as well as peripheral arteries such as the carotid and femoral arteries. The present invention is particularly suited to bypass of the coronary artery.

Synthetic vascular graft tubing is well known and many different constructions based on a variety of materials are available. Typically, such graft tubing is knitted from a polyester yarn such as poly(ethylene terephthalate), sometimes referred to as Dacron. In the known surgical procedures, the synthetic vascular tubing is normally used to bypass a section of diseased vein to maintain blood flow to a patient's extremities and lower limbs.

In the present invention, vascular graft tubing is used in an entirely new way to provide an improvement in arteriovenous bypass grafting procedure. Specifically, it has been found that a porous non-restrictive external stent provided about the bypass vein segment has beneficial effects on the luminal size and the degree of medial and intimal thickening and cell proliferation in a pig vein graft model.

The porous stent used in the invention is normally of synthetic origin, but it could alternatively be formed from a biological material, such as collagen, which would have the advantage that, after a period of time, the stent would be reabsorbed into the body. If a biological material is used, it may be necessary to provide the material with the desired degree of porosity, for example by a technique such as needling.

When the porous graft tubing employed is synthetic, it will typically be of a knitted construction. The synthetic material from which the graft tubing may be formed is preferably a polyester such as poly(ethylene terephthalate), but other synthetic materials would be suitable; indeed any material which is used for implant purposes, and which can be fashioned into a porous tube, is theoretically usable, such as stainless steel, PTFE (high porosity) membrane and fibres, and other metals and polymers.

It is important that the graft tubing used as a stent in this invention is porous, in the sense that it has an ability to be invaded by cells. An indication of porosity can be obtained by using a water permeability test which refers to the rate of flow of water through the wall of the dry prosthesis, and which provides an index of the interstitial leakage rate of the wall. A suitable such test is described in "Practical Cosiderations in Fabric Vascular Grafts" by B. F. Buxton et al, Am. J. Surg. 125:288–293 (1973) in which the dry prosthesis is subjected to an applied head of water of 120 mm Hg, and the volume of water that passes through the wall per minute is measured. The water permeability of the stent in accordance with this test should preferably be at least 5 ml/min/cm$^2$. The preferred maximum water permeability is about 20000 ml/min/cm$^2$. For a typical synthetic grafting material such as Dacron, the water permeability would normally lie in the range of from 150 to 4000 ml/min/cm$^2$. However, for different materials, the relationship between water permeability and their porosity in terms of their use in the present invention varies, and so it is important that, for any given material, experiments are conducted to determine the ideal porosity or water permeability for use in the invention.

In the invention, it is important that the synthetic stent provided externally of the vein segment to be grafted is non-restrictive so as to allow unrestricted expansion of the graft in initial response to arterial pressure. After this initial expansion, it is also believed to be important that the internal diameter of the stent is slightly larger (for example a few mm) than the diameter of the expanded vein. The actual diameter of the stent relative to the vein must be determined empirically bearing these factors in mind, but typically the inner diameter of the stent will be at least about 3 mm larger than the overall outer diameter of the vein segment to be grafted. Normally, the inner diameter of the stent will be no more than about 6 mm larger than the overall outer diameter of the expanded vein graft.

In the surgical procedure of the invention, the vein segment about which the non-restrictive stent is provided is implanted in the normal way in the artery which is to be bypassed. The stent, which is adapted in length to the vein segment to be grafted, is stitched lightly in place. The stent is left in place after the procedure, and becomes incorporated within the growing tissue which surrounds the vein.

Figures 2A, 2B, 2C:
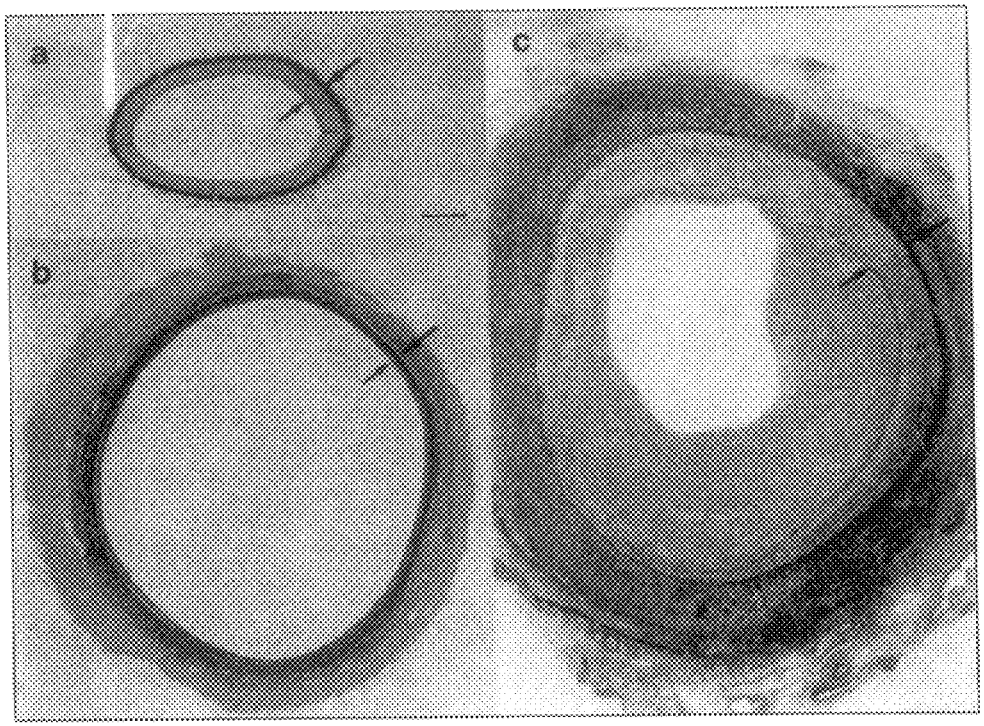
Figures 3A, 3B, 3C:
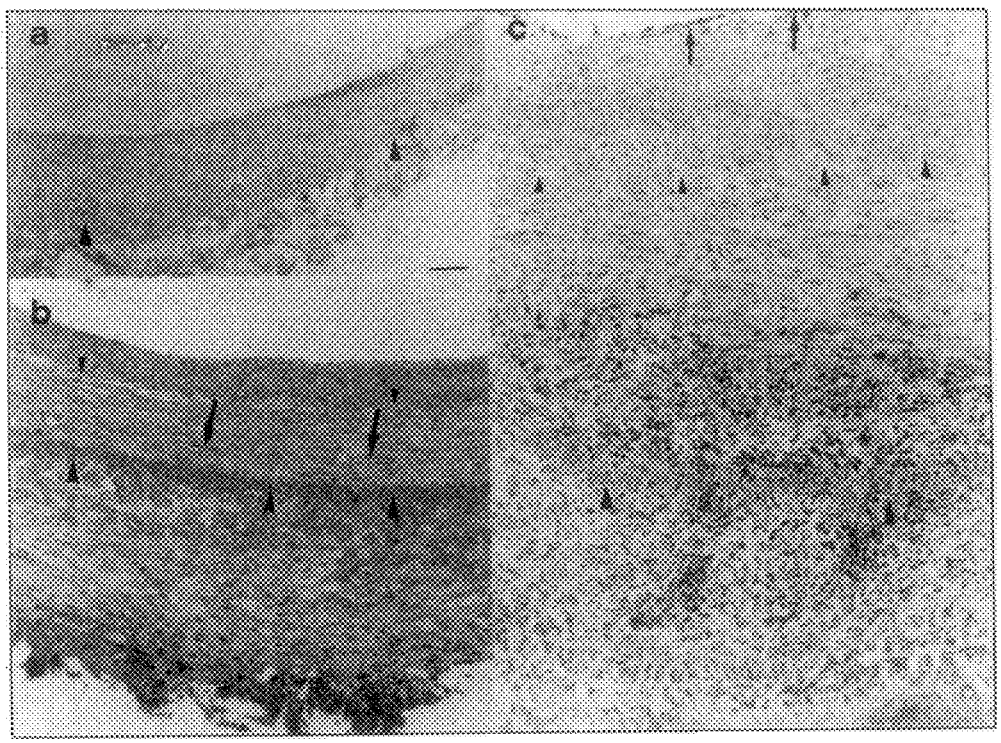

Reference will now be made to the following drawings in which:

FIG. 1 shows a graft stent for use in the present invention;

FIG. 2 shows the histological appearance of (a) an ungrafted vein, (b) a representative unstented graft in a pig model, and (c) a representative stented graft, in a pig model; and FIG. 3 illustrates the immunocytochemistry for proliferating cell nuclear antigen in respect of (a) an ungrafted vein, (b) a representative unstented graft in a pig model, and (c) a representative stented graft in a pig model.

White Land Race pigs (n=9, weighing 20 to 25 kg) were subjected to premedication, anaesthesia and autologous saphenous vein into common carotid artery bypass grafting by a modification of the method described previously. In brief, segments of saphenous vein were dissected using a 'no-touch' technique, rinsed in isoosmotic sodium chloride solution (0.9 g.L$^{-1}$) containing 2 IU/mL heparin and 50 µg/mL glyceryl trinitrate and stored in the same solution at room temperature (23° C.) until needed. Both common carotid arteries of the pigs were exposed. A 3 cm segment of one artery at a time was removed and replaced with a segment of saphenous vein cut sufficiently to allow implantation without longitudinal stretching.

Anastomoses were performed end-to-end with reversed vein, bevelled at 45° using continuous 7-0 prolene sutures. Proximal anastomoses were always performed first; in the case of stented grafts, using a stent as shown in FIG. 1, the vein segments were passed through the stent before completing the distal anastomosis. The stent shown in FIG. 1 comprises a continuous 6 mm diameter VP1200 polyester locknit tube externally supported with helically wound 0.8 mm polypropylene and is available from Vascutek Limited, Inchinnan, Renfrewshire, UK. The stent was cut to a slightly greater length than the graft and held in position by two single 7-0 prolene stitches placed in the adventitia of the artery at each end. The entire procedure took 50 minutes with the order of implantation of stented and unstented grafts randomised between pigs. The use of the distal or proximal portions of the veins for stented or unstented grafts was also randomised.

The animals were allowed to recover and fed a normal chow diet of 4 weeks. The grafts were then removed, pressure fixed ex-vivo at 100 mmHg for 10 mins using 10% buffered formal saline and then post-fixed in the same solution for approximately 24 hours and then processed for wax embedding.

FIG. 2 illustrates the histological appearance of ungrafted saphenous vein, unstented and stented grafts. Transverse (5 $\mu$m) sections were stained with alcian blue Miller's elastin van Gieson stain and examined under light microscopy:

a) an ungrafted vein;

b) a representative stented graft:

c) a representative unstented graft.

Small arrows indicate the position of the internal elastic lamina and large arrows the external elastic lamina. The scale bar relates to all panels and represents 0.5 mm.

FIG. 3 illustrates immunocytochemistry for proliferating cell nuclear antigen a) an ungrafted vein.

b) a representative unstented graft. Note the presence of PCNA positive cells (small arrows) in the neointima close to the luminal surface.

c) a representative stented graft. Note the presence of *vasa vasorum* (large arrows).

Small triangles indicate the position of the internal elastic lamina and large triangles the external elastic lamina. The scale bar relates to all panels and represents 0.5 mm.

Proliferating cell nuclear antigen was detected by immunocytochemistry as described previously. Briefly, a primary monoclonal antibody (PC10, Dako Ltd, High Wycombe, Bucks, HP13 5RE, UK) was used at a 1/100 dilution. This was followed by a 1/50 dilution of biotinylated anti-mouse IgG (Dako) and avidin-biotin-peroxidase conjugate (Dako) according to the manufacturers instructions. Sections were counterstained with Harris' haematoxylin. Strongly positive cells were counted in 5 fields per section using a ×40 objective.

The following table shows the results obtained in terms of the various dimensions of saphenous vein, unstented and stented grafts:

| Parameter | Ungrafted vein | Non-stented graft | Stented graft | p stented vs. non-stented |
|---|---|---|---|---|
| Total cross-sectional area $mm^2$ | 3.7 ± 1.2 | 18.0 ± 5.8 | 13.9 ± 5.9 | 0.1 |
| Luminal area $mm^2$ | 2.5 ± 1.2 | 7.6 ± 3.4 | 11.2 ± 6.2 | <0.05 |
| Medial area $mm^2$ | 1.2 ± 0.9 | 6.55 ± 2.62 | 1.62 ± 0.52 | <0.001 |
| Intimal area $mm^2$ | 0 | 3.84 ± 3.3 | 1.06 ± 0.37 | <0.001 |
| Intimal encroachment (%) | 0 | 33.2 ± 19.1 | 13.3 ± 13.4 | <0.005 |
| Total wall thickness mm | 0.13 ± 0.06 | 0.85 ± 0.38 | 0.25 ± 0.14 | <0.001 |
| Medial thickness mm | 0.13 ± 0.06 | 0.49 ± 0.22 | 0.14 ± 0.08 | <0.001 |
| Intimal thickness mm | 0 | 0.35 ± 0.24 | 0.10 ± 0.07 | <0.001 |

Transverse sections obtained as described in the legend to FIG. 2 were analysed by computer-aided planimetry (MicroScale TM/TC image analysis system, Digithurst Ltd, Royston, Herts, UK), as described previously. Briefly, lumenal, intimal and medial perimeters and areas were computed using the lumenal boundary, internal and external elastic laminae as delimiters. Average intimal, medial and vessel wall thickness were derived from the area and perimeter data. Values are expressed as mean±S.D. and were compared using the Mann-Whitney test.

As described above segments of autologous saphenous vein were implanted into the common carotid arteries of pigs. A porous polyester stent (as shown in FIG. 1) was placed around one graft while the contralateral graft served as a control. The lumenal diameter of pig saphenous vein measured in situ before implantation by echocardiographic ultrasonography was 1.6±0.1 mm (SEM, n=9). Immediately after grafting into the common carotid artery the diameter of stented or unstented veins increased to 3.6±0.2 mm. This was approximately 2 mm smaller than the internal diameter of the stent.

All grafts whether stented or not were patent 4 weeks after implantation. As illustrated in FIG. 2 and summarised in the Table, stented and unstented grafts had a similar total (lumen plus wall) cross-sectional area that was approximately 4 times greater than that of the original vein. This confirmed that the stent allowed expansion of the graft in response to arterial pressure. Unstented grafts showed an increase in luminal area compared to ungrafted vein. However, medial enlargement, fragmentation of the internal elastic lamina and the development of a neointima also occurred (FIG. 2, Table), in agreement with previous observations. Stented grafts had a significantly greater final lumenal area than unstented grafts because there was no medial enlargement compared to ungrafted vein and neointima formation was dramatically reduced almost 4-fold compared to unstented grafts. As a result, the encroachment of the intima into the lumen was reduced by stenting from 33 to 13% (FIG. 2, Table).

The presence of cells progressing through the cell cycle was detected by immunocytochemistry for proliferating cell nuclear antigen (PCNA). PCNA positive cells were rarely detected in ungrafted vein but were abundant in the media and the most lumenal aspect of the neointima of unstented grafts (FIG. 3). The medial PCNA index was reduced by stenting from 21±4% to 2.4±2.2% (n=9, p<0.001). The neointimal PCNA index was also reduced by stenting from 24±4% to 7±3% (p<0.01). PCNA labelling in the neoadventitia was observed in both stented and unstented grafts (FIG. 3). The presence of microvessels penetrating the media of stented grafts can also be noted from FIG. 3. There were endothelial cells lining these vessels, as confirmed by staining for *Dolichos Bifluoros* lectin (results not shown). Such vessels were absent from the media of ungrafted vein or unstented grafts.

What is claimed is:

1. An arteriovenous bypass grafting procedure comprising:

enveloping a vein segment having an outer diameter with a porous external stent having an inner diameter larger than the vein segment's outer diameter;

grafting the enveloped vein segment into the arterial circulation system of a mammalian subject; and establishing arterial blood flow through the grafted vein segment, wherein the inner diameter of the stent is sufficiently larger than the outer diameter of the vein segment to allow unrestricted expansion of the vein segment in response to arterial circulation.

2. An arteriovenous bypass grafting procedure according to claim 1, wherein the vein segment about which said porous stent is provided is implanted in one of the following: the coronary artery or in a peripheral artery.

3. An arteriovenous bypass grafting procedure according to claim 1, wherein said porous stent comprises a synthetic material.

4. An arteriovenous bypass grafting procedure according to claim 3, wherein the porous stent is of a knitted construction.

5. An arteriovenous bypass grafting procedure according to claim 3, wherein the synthetic material is a polyester.

6. An arteriovenous bypass grafting procedure according to claim 5, wherein the synthetic material is a poly(ethylene terephtalate).

7. An arteriovenous bypass grafting procedure according to claim 1, wherein said porous stent comprises a biological material.

8. An arteriovenous bypass grafting procedure according to claim 1, wherein the water permeability of the stent is at least 5 ml/min/cm$^2$.

9. An arteriovenous bypass grafting procedure according to claim 1, wherein the water permeability of the stent is no greater than about 20000 ml/min/cm$^2$.

10. An arteriovenous bypass grafting procedure according to claim 1, wherein the water permeability of the stent is in the range of from 150 to 4000 ml/min/cm$^2$.

11. An arteriovenous bypass grafting procedure according to claim 1, wherein the inner diameter of the stent is at least about 3 mm larger than the outer diameter of the vein segment to be grafted.

12. An arteriovenous bypass grafting procedure according to claim 1, wherein the inner diameter of the stent is no more than about 6 mm larger than the outer diameter of the expanded vein segment.

13. The procedure according to claim 1 wherein the grafting of the vein segment comprises attaching one end of the vein segment to an artery prior to introducing the external stent around the vein segment.

14. The arteriovenous bypass grafting procedure according to claim 1, wherein the inner diameter of the stent is greater than a potential maximum outer diameter of the vein segment in response to initial arterial circulation.

15. An arteriovenous bypass grafting procedure of claim 1, further comprising selecting the inner diameter of the stent of a size appropriate to create a cellular invasion region between the outer diameter of the vein segment and the inner diameter of the stent.

16. The arteriovenous bypass grafting procedure of claim 1, further comprising selecting an inner diameter of the stent that is greater than a maximum outer diameter of the vein segment during arterial circulation through the vein segment.

17. The arteriovenous bypass grafting procedure of claim 1, wherein the grafting and enveloping steps occur at substantially the same time.

18. An externally stented vein segment structure for use in an arteriovenous bypass grafting procedure, the structure comprising:

a vein segment having an outer diameter and grafted into the arterial circulation system of a mammalian subject; and a porous stent, having an inner diameter larger than the vein seqment's outer diameter, provided about said vein segment, the stent's inner diameter being sufficiently larger than the vein segment's outer diameter to allow unrestricted expansion of the vein segment in response to arterial circulation within the mammalian subject.

19. An externally stented vein segment according to claim 18, wherein said porous stent comprises a synthetic material.

20. An externally stented vein segment according to claim 19, wherein the porous stent is of a knitted construction.

21. An externally stented vein segment according to claim 19, wherein the synthetic material is a polyester.

22. An externally stented vein segment according to claim 19, wherein the synthetic material is a poly(ethylene terephtalate).

23. An externally stented vein segment according to claim 18, wherein said porous stent comprises a biological material.

24. An externally stented vein segment according to claim 18, wherein the water permeability of the stent is at least 5 ml/min/cm$^2$.

25. An externally stented vein segment according to claim 18, wherein the water permeability of the stent is no greater than about 20000 ml/min/cm$^2$.

26. The externally stented vein segment structure of claim 18, wherein the inner diameter of the stent is greater than a potential maximum outer diameter of the vein segment in response to initial arterial circulation.

27. The externally stented vein segment structure of claim 18, wherein the inner diameter of the stent is at least about 3 mm larger than the outer diameter of the vein segment.

28. The externally stented vein segment structure of claim 18, further comprising selecting the inner diameter of the stent of a size appropriate to create a cellular invasion region between the outer diameter of the vein segment and the inner diameter of the stent.

29. The externally stented vein segment structure of claim 18, further comprising selecting the inner diameter of the stent so that it is greater than a maximum outer diameter of the vein segment during arterial circulation through the vein segment.

30. An arteriovenous bypass grafting procedure comprising:

grafting a vein segment into the arterial circulation system of a mammalian subject; and establishing arterial blood flow through the grafted vein segment, wherein, prior to the completion of said grafting step, a porous external stent having an inner diameter larger than an outer diameter of the vein segment is introduced about the vein segment, wherein the inner diameter of the stent is at least 3 mm larger than the outer diameter of the vein segment, thereby allowing unrestricted expansion of the vein segment in response to initial arterial pressure, and wherein the cellular invasion region is created between the outer diameter of the vein segment and the inner diameter of the stent.

31. An arteriovenous bypass grafting procedure comprising:

grafting a vein segment into the arterial circulation system of a mammalian subject; and establishing arterial blood flow through the grafted vein segment, wherein, prior to the completion of said grafting step, a porous external stent having an inner diameter larger than an outer diameter of the vein segment is introduced about the vein segment, wherein the inner diameter of the stent is sufficiently larger than the outer diameter of the vein segment to create a cellular invasion cavity, and wherein, once arterial blood flow is established through the grafted vein segment, cells are permitted to accumulate and reorganize over time in the cellular invasion cavity to provide support for the grafted vein segment.

32. An arteriovenous bypass grafting procedure comprising:

grafting a vein segment into the arterial circulation system of a mammalian subject; and establishing arterial blood flow through the grafted vein segment, wherein, prior to the completion of said grafting step, a porous external stent having an inner diameter larger than an outer diameter of the vein segment is introduced about the vein segment, and wherein the inner diameter of the stent is sufficiently larger than the outer diameter of the vein segment to allow unrestricted expansion of the vein segment in response to arterial circulation.

* * * * *